(12) United States Patent
Makiura et al.

(10) Patent No.: US 8,987,439 B2
(45) Date of Patent: Mar. 24, 2015

(54) THREE-DIMENSIONAL STRUCTURE AND METHOD OF PRODUCING THE SAME

(75) Inventors: Rie Makiura, Osaka (JP); Hiroshi Kitagawa, Nara (JP)

(73) Assignee: Japan Science and Technology Agency, Saitama (JP)

( * ) Notice: Subject to any disclaimer, the term of this patent is extended or adjusted under 35 U.S.C. 154(b) by 13 days.

(21) Appl. No.: 13/521,343

(22) PCT Filed: Jan. 13, 2011

(86) PCT No.: PCT/JP2011/000144
§ 371 (c)(1),
(2), (4) Date: Jul. 10, 2012

(87) PCT Pub. No.: WO2011/086931
PCT Pub. Date: Jul. 21, 2011

(65) Prior Publication Data
US 2012/0296083 A1    Nov. 22, 2012

(30) Foreign Application Priority Data
Jan. 18, 2010  (JP) ................. 2010-007801

(51) Int. Cl.
*C07D 487/22* (2006.01)
*C07D 213/16* (2006.01)

(52) U.S. Cl.
CPC ........... *C07D 213/16* (2013.01); *C07B 2200/11* (2013.01); *C07D 487/22* (2013.01)
USPC .......................................................... 540/145

(58) Field of Classification Search
CPC .................................................. C07D 487/22
USPC ....................................................... 540/145
See application file for complete search history.

(56) References Cited

U.S. PATENT DOCUMENTS

2007/0219280 A1    9/2007  Kitagawa et al.

FOREIGN PATENT DOCUMENTS

| JP | 2004-067596 | 3/2004 |
| JP | 2004-238347 | 8/2004 |
| JP | 2005-255651 | 9/2005 |
| JP | 2007-063448 | 3/2007 |

OTHER PUBLICATIONS

Motoyama, et al., "Fabrication of a surface coordination polymer with a porphyr in derivative on a solid substrate", Proceedings of the 89th Annual Spring Meeting of Chemical Society of Japan, 1, p. 199, 3D3-02, 2009.
Shmilovits, et al., "Coordination Polymers of Tetra(4-carboxyphenyl)porphyrins Sustained by Tetrahedral Zinc Ion Linkers", Crystal Growth & Design, vol. 4, No. 3. pp. 633-638, 2004.
Kosal, et al., "A functional zeolite analogue assembled from metalloporphyrins", Nature Materials, vol. 1, No. 2, pp. 118-121, Supplementary Information, 2002.
Choi, et al., "Pillared Porphyrin Homologous Series: Intergrowth in Metal—Organic Frameworks", Inorganic Chemistry, vol. 48, No. 2, pp. 426-428, 2009.
Makiura, et al., "Surface nano-architecture of a metal-organic framework", Nature Materials, vol. 9, Jul. 2010, pp. 565-571.

*Primary Examiner* — Brian McDowell
(74) *Attorney, Agent, or Firm* — Hamre, Schumann, Mueller & Larson, P.C.

(57) ABSTRACT

The three-dimensional structure of the present invention is a three-dimensional structure formed on a base. This three-dimensional structure contains a plurality of porphyrins, a plurality of first metal ions, and a plurality of specific organic molecules. The porphyrin contains two or more functional groups. The first metal ion is a metal ion for linking the functional group of one porphyrin to the functional group of another porphyrin. The above specific organic molecule is an organic molecule that forms a coordinate bond with a metal ion contained in the two-dimensional structure and that has only one site to coordinate to the metal ion.

12 Claims, 9 Drawing Sheets

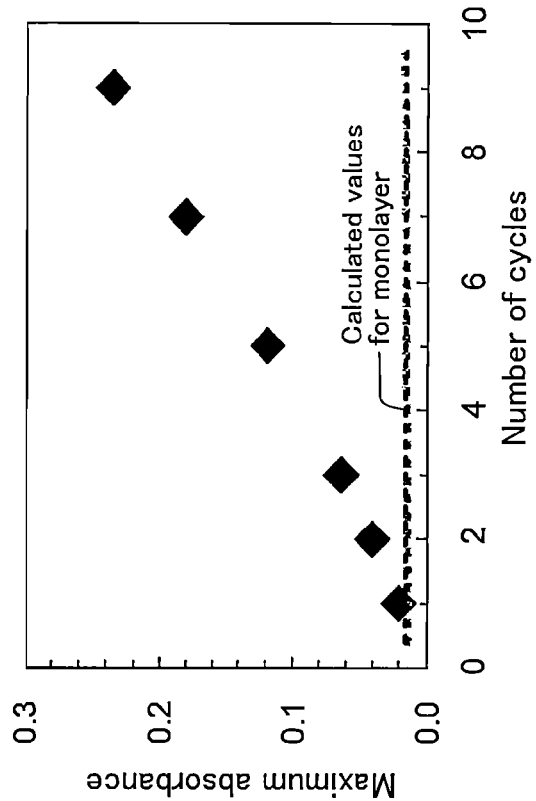
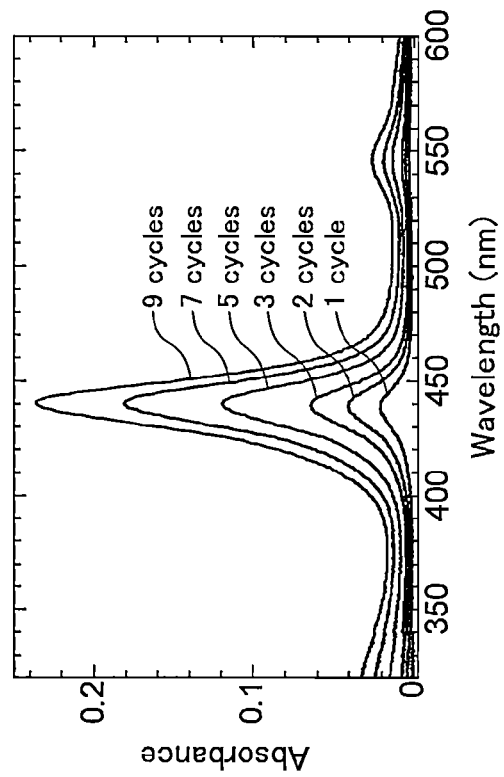
Fig. 4B
Fig. 4A

THREE-DIMENSIONAL STRUCTURE AND METHOD OF PRODUCING THE SAME

TECHNICAL FIELD

The present invention relates to three-dimensional structures and methods of producing the same.

BACKGROUND ART

Coordination polymers and organometallic complexes have been conventionally studied because they exhibit optically, magnetically and electrochemically interesting properties. For example, an organometallic complex structure and a coordination polymer structure have been proposed (for example, JP 2005-255651 A and JP 2007-63448 A). A method of fabricating a three-dimensional structure in a solution also has been proposed (Eun-Young Choi, et al., "Pillared Porphyrin Homologous Series: Intergrowth in Metal-Organic Frameworks", Inorganic Chemistry, Vol. 48, No. 2, Pages 426-428, 2009).

CITATION LIST

Patent Literature

Patent Literature 1 JP 2005-255651 A
Patent Literature 2 JP 2007-63448 A

Non-Patent Literature

Non-Patent Literature 1 Eun-Young Choi, et al., "Pillared Porphyrin Homologous Series: Intergrowth in Metal-Organic Frameworks", Inorganic Chemistry, Vol. 48, No. 2, Pages 426-428, 2009

SUMMARY OF INVENTION

Technical Problem

In the above conventional art, however, the structures are each formed by mixing its component materials in a solution, which makes it difficult to control the size and position of the structure. For the application of such a structure to a device, it is important to form the structure on a substrate, but the structure is not formed on a substrate in the above conventional method.

Under these circumstances, one of the objects of the present invention is to provide a size- and shape-controlled three-dimensional structure formed on a base and a method of producing the structure.

Solution to Problem

In order to achieve the above object, the present invention provides a three-dimensional structure formed on a base. This three-dimensional structure includes stacked two-dimensional structures. The two-dimensional structure contains a plurality of porphyrins, a plurality of first metal ions, and a plurality of specific organic molecules. The porphyrin contains two or more functional groups, the first metal ion is a metal ion for linking the functional group of one porphyrin to the functional group of another porphyrin, and the specific organic molecule is an organic molecule that forms a coordinate bond with a metal ion contained in the two-dimensional structure and that has only one site to coordinate to the metal ion.

The present invention also provides a method of producing a three-dimensional structure. This production method includes the steps of: (i) forming a two-dimensional structure on the surface of a liquid; (ii) depositing the two-dimensional structure on a base; and (iii) repeating a cycle including the step (i) and the step (ii) once or more. The two-dimensional structure contains a plurality of porphyrins, a plurality of first metal ions, and a plurality of specific organic molecules. The porphyrin contains two or more functional groups, the first metal ion is a metal ion for linking the functional group of one porphyrin to the functional group of another porphyrin, and the specific organic molecule is an organic molecule that forms a coordinate bond with a metal ion contained in the two-dimensional structure and that has only one site to coordinate to the metal ion.

Advantageous Effects of Invention

According to the present invention, a size- and shape-controlled three-dimensional structure formed on a base can be obtained. A crystalline three-dimensional structure also can be obtained by selecting appropriate materials.

BRIEF DESCRIPTION OF DRAWINGS

FIG. 4A shows the relationship between the number of deposition cycles and the absorption spectrum.

FIG. 4B shows the relationship between the number of deposition cycles and the maximum absorbance.

FIGS. 5($c$) and ($d$) show the absorption spectra of CoTCPP- and pyridine-containing films formed on the surface of a cupric chloride aqueous solution and the surface of pure water.

FIGS. 7($c$) to ($e$) show a model of a three-dimensional structure.

DESCRIPTION OF EMBODIMENTS

Figure 1A:
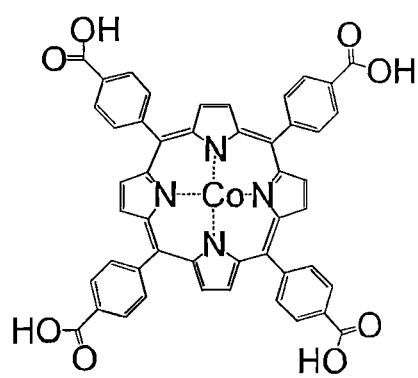
FIG. 1A shows an example of the compound used in the present invention.

Hereinafter, embodiments of the present invention will be described with examples. The present invention is not limited to the following embodiments and examples. In the following description, specific numerical values or specific materials may be given by way of examples, but other numerical values or other materials may be used as long as the effects of the present invention can be obtained. In the following drawings, metal ions may be shown as atoms.

(Production Method of Three-Dimensional Structure)

The method of the present invention is a method of producing a three-dimensional structure. According to this production method, a three-dimensional structure formed on a base can be obtained. This production method includes the following steps (i), (ii) and (iii).

In the step (i), a two-dimensional structure is formed on the surface of a liquid. The two-dimensional structure contains a plurality of porphyrins, a plurality of first metal ions, and a plurality of specific organic molecules. Hereinafter, the porphyrin contained in the two-dimensional structure is sometimes referred to as a "component (A)", and the specific organic molecule is sometimes referred to as a "pillar molecule". The component (A) contains two or more (for example, three or four) functional groups. The first metal ion is a metal ion for linking the functional group of one component (A) to the functional group of another component (A). Specifically, the first metal ion links the functional groups of the neighboring components (A) via the first metal ion itself. The pillar molecule is an organic molecule that forms a coordinate bond with a metal ion contained in the two-dimensional structure and that has only one site to coordinate to the metal ion. A typical example of the two-dimensional structure is composed of organometallic complexes, first metal ions, and pillar molecules.

In this description, examples of "porphyrin" include a porphyrin molecule that is not in the form of a metal complex and a porphyrin metal complex. When the porphyrin (component (A)) is a porphyrin metal complex, examples of the central metal ion that coordinates to the porphine ring (porphyrin ring) include transition metal ions (for example, cobalt ion and palladium ion). Examples of the functional group in the component (A) include carboxyl group, dithiocarboxyl group, and thioamide group.

Examples of the first metal ion include polyvalent metal ions (for example, divalent metal ions). Examples of the first metal ion include transition metal ions, for example, copper ion. The first metal ion may be divalent copper ion or divalent nickel ion. Examples of the combination of the functional group in the component (A) and the first metal ion for linking (cross-linking) the functional groups include combinations of carboxyl group and copper ion, carboxyl group and cobalt ion, dithiocarboxyl group and nickel ion, dithiocarboxyl group and platinum ion, thioamide group and copper ion, thioamide group and iron ion, and carboxyl group and nickel ion.

When the component (A) does not contain a metal ion, the pillar molecule is a molecule that forms a coordinate bond with the first metal ion. When the component (A) contains a metal ion, the pillar molecule is a molecule that forms a coordinate bond with at least one metal ion selected from the metal ion in the component (A) and the first metal ion. For example, when the component (A) is a porphyrin metal complex, the pillar molecule is a molecule that forms a coordinate bond with at least one metal ion selected from a central metal ion (a second metal ion) of the porphyrin metal complex and the first metal ion. In one example, the pillar molecule coordinates to the central metal ion of the porphyrin metal complex. In another example, the pillar molecule coordinates to the first metal ion, which is a component of a dinuclear paddle wheel structure to be described later.

Examples of the pillar molecule include pyridine, methylpyridine, isoquinoline, and phenylpyridine. Examples of the combination of a pillar molecule and a metal ion to which the pillar molecule coordinates include combinations of pyridine and cobalt ion, pyridine and copper ion, phenylpyridine and cobalt ion, and phenylpyridine and copper ion. Preferably, the number of sites that are contained in the pillar molecule and that coordinate to the metal ion is one. Preferably, the pillar molecule is a molecule that is oriented in a direction perpendicular or approximately perpendicular to a direction in which the two-dimensional structure extends (hereinafter sometimes referred to as an "in-plane direction"). Examples of the pillar molecule do not include pyrazine or 4,4'-bipyridine having two or more sites to coordinate to metal ions. However, a molecule even having two or more atomic groups that can coordinate to metal ions falls within the pillar molecule if the structure of the molecule allows only one of the sites to coordinate to the metal ion of the two-dimensional structure.

In the step (ii), the two-dimensional structure formed in the step (i) is deposited on a base. The two-dimensional structure is placed on the base by the step (ii). Examples of the method for forming a two-dimensional structure on the surface of a liquid and depositing the structure on a base include the Langmuir-Blodgett method (LB method). That is, the step (i) and the step (ii) may be performed by the Langmuir-Blodgett method. The LB method is well known as a method for forming a monomolecular film on the surface of a liquid.

There is no particular limitation on the base as long as the two-dimensional structure is to be deposited thereon. Examples of the base include semiconductor substrates (for example, a silicon substrate), substrates made of inorganic materials such as quartz substrates, glass substrates and metal substrates (for example, a gold substrate), graphite substrates, and resin substrates.

In the step (iii), a cycle (hereinafter sometimes referred to as a "deposition cycle") including the step (i) and the step (ii) is repeated once or more. The two-dimensional structures are stacked on the base by the step (iii). There is no particular limitation on the number of deposition cycles, and the number of cycles can be determined for the intended purpose. The thickness of the three-dimensional structure can be controlled by the number of deposition cycles. The number of deposition cycles performed in the step (iii) may be determined in the range of 1 to 100 (for example, 5 to 20). When the step (i) and the step (ii) are performed only once without performing the step a two-dimensional structure formed on the base is obtained.

The production method of the present invention may include, after the step (ii), a step (x) of immersing the base on which the two-dimensional structure is deposited into a solvent. In this case, the step (iii) is a step of repeating a cycle (a deposition cycle) including the step (i), the step (ii) and the step (x) once or more. It is desired that the solvent used in the step (x) be a solvent that dissolves the first metal ions and that does not break any of the bond between the component (A) and the first metal ion, the coordinate bond between the pillar molecule and the first metal ion, and the coordinate bond between the pillar molecule and the metal ion in the component (A). Examples of the solvent include pure water and ethanol.

In one example of the production method of the present invention, porphyrin (component (A)) may contain four carboxyl groups. Specifically, the porphyrin may be a porphyrin containing four carboxyl groups but not containing a central metal ion coordinated to a porphine ring, or may be a porphyrin metal complex containing four carboxyl groups and a central metal ion coordinated to a porphine ring. In one example, the component (A) is a porphyrin molecule (a porphyrin that is not in the form of a metal complex) containing four carboxyl groups, and the first metal ion is a transition metal ion. In another example, the component (A) is a porphyrin metal complex containing four carboxyl groups and a central metal ion coordinated to a porphine ring, and the first metal ion is a transition metal ion. The central metal ion in the porphyrin metal complex may be a transition metal ion. For example, it may be cobalt ion.

Figure 1B:
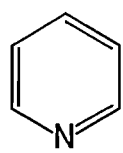
FIG. 1B shows another example of the compound used in the present invention.

FIG. 1A shows a porphyrin metal complex containing four carboxyl groups and a cobalt ion. Hereinafter, 5,10,15,20-tetrakis(4-carboxyphenyl)porphyrinato-cobalt (II) in FIG. 1A is sometimes referred to as "CoTCPP". Examples of the pillar molecule containing a nitrogen-containing aromatic ring include pyridine (see FIG. 1B). Hereinafter, pyridine is sometimes referred to as "py".

In the production method of the present invention, the first metal ion may be divalent copper ion or divalent nickel ion, and the pillar molecule may be a molecule containing a nitrogen-containing aromatic ring. For example, the first metal ion may be divalent copper ion, and the pillar molecule may be a molecule containing a nitrogen-containing aromatic ring.

In the production method of the present invention, the pillar molecule may be pyridine.

The step (i) may be a step of forming a two-dimensional structure on the surface of a liquid by adding a second solution containing the components (A) and the pillar molecules to a first solution containing the first metal ions. In one example, the first solution is an aqueous solution, and a solvent in the second solution is an organic solvent.

The concentration of the first metal ions in the first solution may be in the range of 1 mmol/L to 100 mmol/L or in the range of 1 mmol/L to 5 mmol/L.

The step (ii) may be a step of bringing the base closer to (into contact with) the two-dimensional structure, with the surface of the base kept parallel to the surface of the liquid, and thereby depositing the two-dimensional structure on the base. Such a method is sometimes referred to as "horizontal dipping".

The pillar molecule may contain nitrogen. The pillar molecule may contain a π electron. In one example, neighboring two-dimensional structures are fixed together by interactions (for example, π-π interactions) between the pillar molecules that are oriented in a direction perpendicular or approximately perpendicular to the in-plane direction. In this case, the two-dimensional structures can sometimes be moved to slide in the in-plane direction. It is expected that the use of such sliding will allow the three-dimensional structure to have various functions. For example, the size of pores in the three-dimensional structure can be changed by such sliding. More specifically, it is expected that the adsorption of gas molecules on the three-dimensional structure will change the size of the pores in the three-dimensional structure. Such a change allows selective adsorption of molecules or selective reaction control. It should be noted that this sliding of the two-dimensional structure is the effect that can be obtained only by the use of monodentate pillar molecules.

In the conventional method for building a three-dimensional structure in a solution, the three-dimensional structure is built by linking two-dimensional structures in the solution. Therefore, in the conventional method, monodentate pillar molecules cannot be used. On the other hand, the present inventors have found that a combination of specific materials and specific methods makes it possible to build a three-dimensional structure using monodentate pillar molecules. In the method of the present invention, a three-dimensional structure is formed by stacking two-dimensional structures formed on the surface of a liquid. Therefore, unlike the conventional method, the method of the present invention allows a three-dimensional structure to be formed using monodentate pillar molecules. In the method of the present invention, the number of two-dimensional structures to be stacked can be adjusted by the number of cycles, each including the step (i) and the step (ii), to be performed. That is, according to the method of the present invention, the thickness of the three-dimensional structure can be controlled easily. The thickness of the three-dimensional structure fabricated by the method of the present invention may be in the range of 10 nm to 100 nm.

(Three-Dimensional Structure)

The three-dimensional structure of the present invention can be produced by the above production method of the present invention. Since the details of the production method of the present invention that have been described can be applied to the three-dimensional structure of the present invention, the same description may be omitted. Furthermore, the details of the three-dimensional structure of the present invention that have been described can be applied to the production method of the present invention.

The three-dimensional structure of the present invention is formed on a base. The three-dimensional structure includes stacked two-dimensional structures. The two-dimensional structure contains a plurality of porphyrins (components (A)), a plurality of first metal ions, and a plurality of specific organic molecules (pillar molecules). The porphyrin contains two or more functional groups. The first metal ion is a metal ion for linking the functional group of one porphyrin to the functional group of another porphyrin. The pillar molecule is an organic molecule that forms a coordinate bond with a metal ion contained in the two-dimensional structure and that has only one site to coordinate to the metal ion. Since the porphyrin (component (A)), the first metal ion, and the pillar molecule have been described above, the same description may be omitted.

As described above, the porphyrin (component (A)) may contain four carboxyl groups. Specifically, the porphyrin may be a porphyrin containing four carboxyl groups but not containing a central metal ion coordinated to a porphine ring, or may be a porphyrin metal complex containing four carboxyl groups and a central metal ion coordinated to a porphine ring. In one example of this case, the carboxyl groups of neighboring porphyrins (components (A)) are cross-linked by the first metal ions (for example, transition metal ions). Such a cross-linked structure is sometimes referred to as a dinuclear paddle wheel structure.

EXAMPLES

Examples in which the three-dimensional structures of the present invention were produced are described below.

Example 1

In Example 1, CoTCPP (manufactured by Porphyrin Systems) was used as components (A). Cupric chloride dihydrate ($CuCl_2 \cdot 2H_2O$) was used as a compound containing the first metal ion. Pyridine was used as the pillar molecule. For the X-ray diffraction measurement (XRD) and atomic force microscope (AFM) measurement, a silicon single crystal substrate ((100) plane) was used as a substrate. For the ultraviolet-visible absorption spectrum measurement, a quartz substrate was used as a substrate. These substrates were subjected to ultrasonic cleaning in chloroform, acetone, and ethanol, each for 30 minutes, before two-dimensional structures are stacked in layers thereon.

First, 8.5 mg of CoTCPP and 20 µL of pyridine were dissolved in 50 mL of chloroform/methanol mixed solvent. The volume ratio of chloroform and methanol was 3:1. A PTFE trough (with dimensions of 375×75×5 mm and a capacity of 0.16 L) was filled with an aqueous solution of cupric chloride dihydrate (with a concentration of 0.1 M). A film formation apparatus including this trough is provided with two opposing barrier bars. The surface of the aqueous solution in the trough was cleaned by aspiration.

Next, 96 μl of CoTCPP/pyridine solution was spread with a microsyringe between the two barrier bars on the surface of the cupric chloride solution. Next, the two barriers were moved closer to each other at a rate of 10 mm/min while measuring the surface pressure. A film (two-dimensional structure) was formed on the surface of the aqueous solution in this manner (Step (i)). Then, the film at a surface pressure of 5 mNm$^{-1}$ was transferred to the substrate (Step (ii)). The film was transferred to the substrate by bringing the substrate into contact with the film with the surface of the substrate kept parallel to the surface of the aqueous solution (the surface of the film). Next, the substrate was rinsed with distilled water for 3 minutes, immersed in distilled water for 3 minutes, and dried by blowing nitrogen. A film (a two-dimensional structure) composed of CoTCPP, copper ion, and pyridine was formed on the substrate in this manner.

Figure 2:
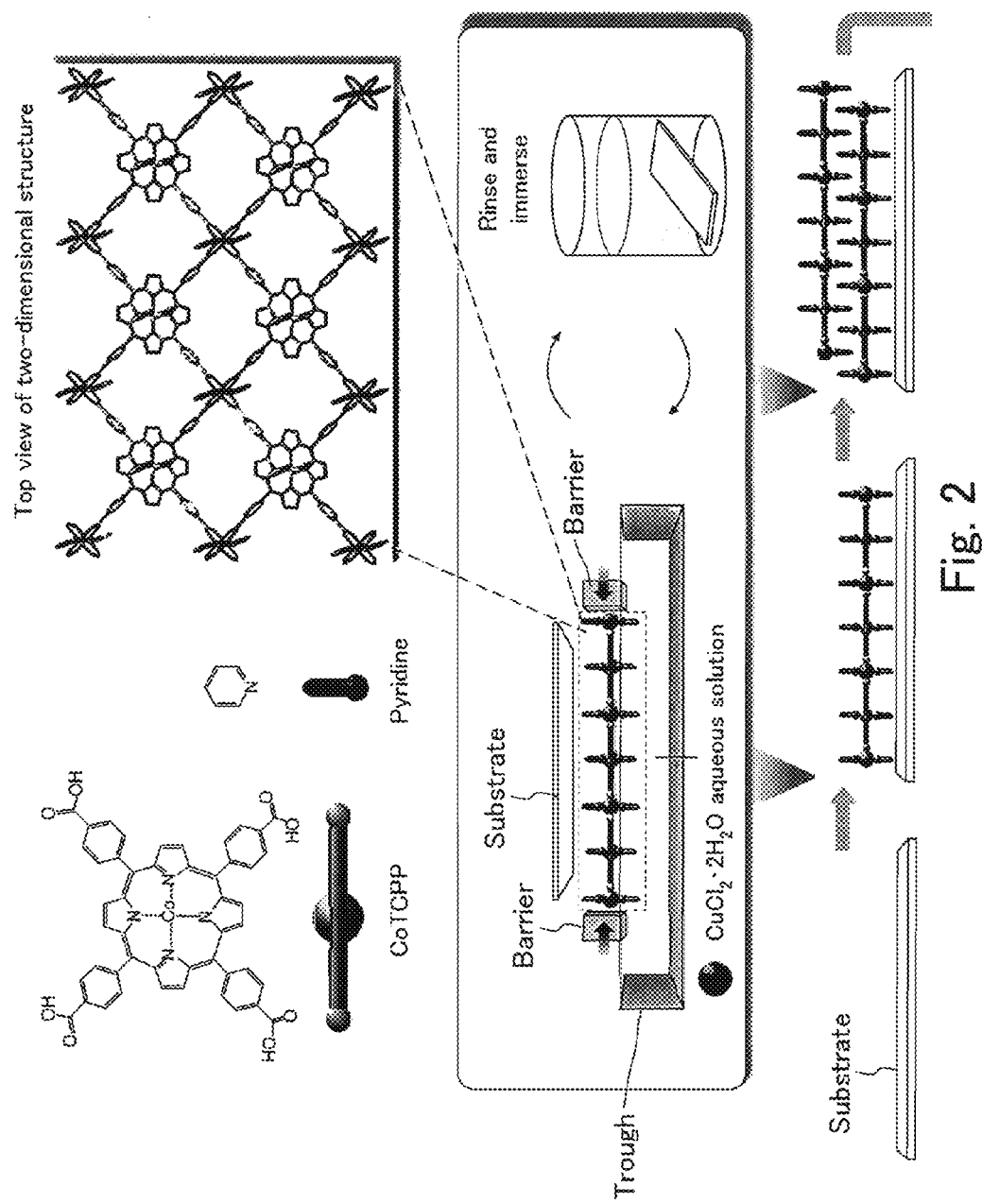
FIG. 2 schematically shows the production method of the present invention.

Next, a step including, as one cycle, the above step (i), step (ii), and rinsing/immersing/drying was performed repeatedly. Thereby, a three-dimensional structure including stacked two-dimensional structures was formed on the substrate. FIG. 2 shows these steps schematically.

Comparative Example 1

In Comparative Example 1, the same processes were carried out as in Example 1, except that pure water was used instead of the aqueous solution of cupric chloride dihydrate. Specifically, pure water was placed in a trough, and 160 μL of CoTCPP/pyridine solution was spread on the surface of the pure water. The other processes were carried out in the same manner as in Example 1.

Figure 3:
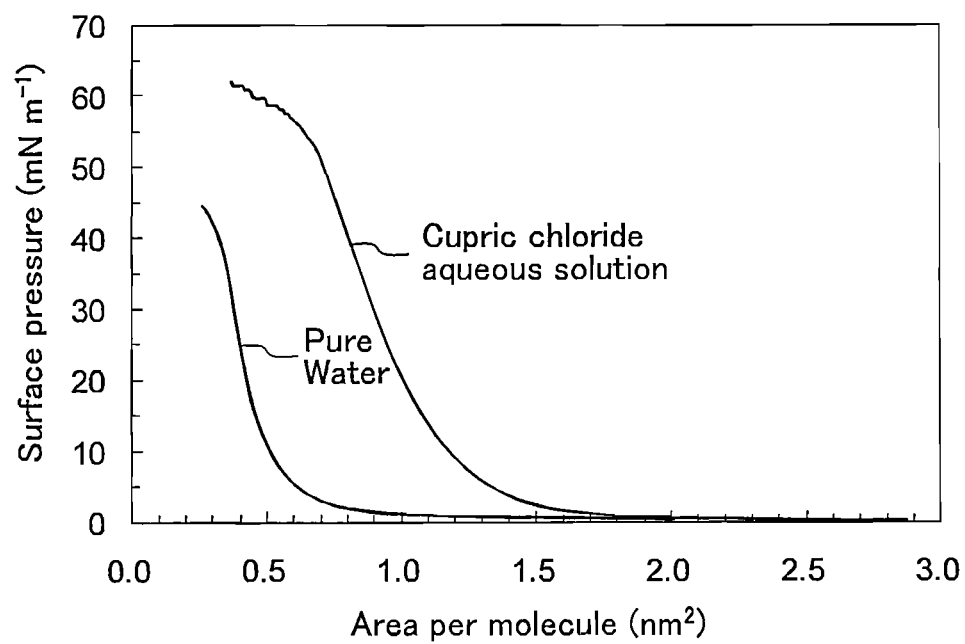
FIG. 3 is a diagram showing the areas per porphyrin metal complex molecule in the presence and absence of cupric chloride.

FIG. 3 shows the relationship between the area per porphyrin metal complex and the surface pressure in each of the case using the aqueous solution of cupric chloride dihydrate and the case of using pure water. At the same surface pressure, the area per molecule was larger in Example 1 where the aqueous solution of cupric chloride was used. This suggests that CoT-PPs are cross-linked by copper ions by the use of the aqueous solution of cupric chloride and that a two-dimensional structure is formed on the surface of the liquid.

(Ultraviolet-Visible Absorption Spectrum Measurement)

FIG. 4A shows a change in the absorption spectrum with a change in the number of stacked two-dimensional structures. FIG. 4B shows a change in the height of the absorption peak at about 440 nm (the Soret band). In these diagrams, the number of cycles being 1 (one cycle) means that only one two-dimensional structure layer is formed on the base.

The calculated value for the monolayer shown in FIG. 4B is a value obtained by considering the absorption coefficient of porphyrin and the orientation of the molecule. This value is in good agreement with the actual measured value for one cycle, that is, the actual measured value for only one two-dimensional structure layer formed on the substrate. This suggests that the surface of the substrate is sufficiently covered with a CoTCPP-py-Cu monolayer. Furthermore, as shown in FIG. 4B, the height of the absorption peak is proportional to the number of cycles. This suggests that the number of stacked two-dimensional structures increases one by one in each cycle.

Figure 5:
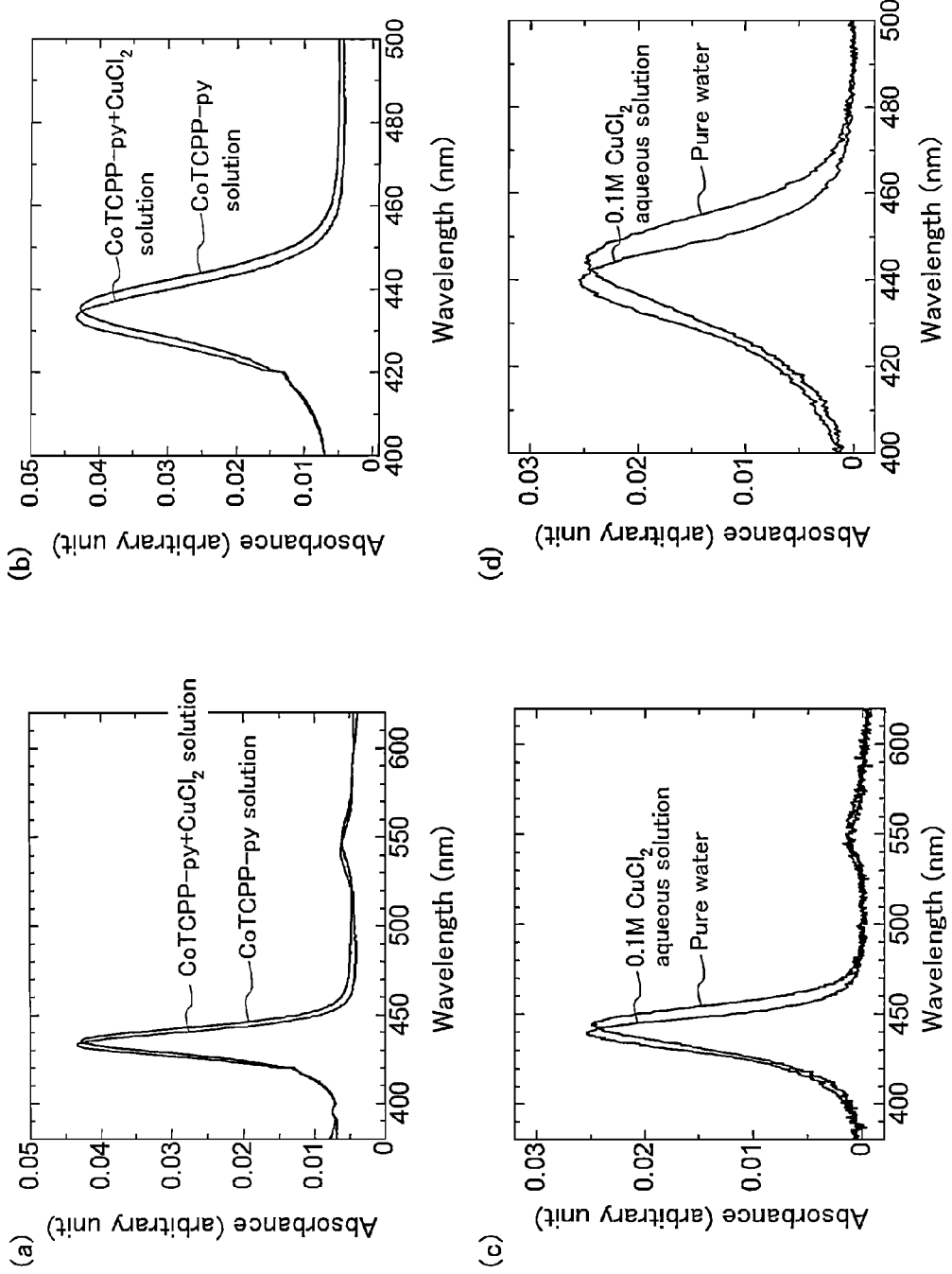
FIGS. 5($a$) and ($b$) show the absorption spectra of CoTCPP-pyridine solutions in the presence and absence of cupric chloride.

For reference, FIGS. 5(a) and (b) show the absorption spectra in solutions. FIG. 5(a) shows the absorption spectra of CoTCPP-pyridine (py) solutions in the presence and absence of CuCl$_2$. The solvent is a chloroform/methanol mixed solvent. FIG. 5(b) is diagram showing a selected portion of FIG. 5(a). In the presence of CuCl$_2$, the Soret band at about 440 nm shifts toward shorter wavelengths. This shifts indicates the coordination between the carboxyl groups of CoTCPP and Cu$^{2+}$ ions.

FIG. 5(c) shows the absorption spectra of CoTCPP- and pyridine (py)-containing films formed on the surface of a 0.1 M (mol/L) CuCl$_2$ aqueous solution and the surface of pure water. The film formed on the surface of the aqueous solution was transferred to a quartz substrate and then its absorption spectrum was measured. FIG. 5(d) is a diagram showing a selected portion of FIG. 5(c). As shown in FIG. 5(d), also in the LB film, the Soret band shifts in the same manner as in FIG. 5(b) in the presence of CuCl$_2$. This suggests that constitutional units composed of CoTCPP and pyridine (py) react with Cu$^{2+}$ to form a two-dimensional structure composed of CoTCPP, pyridine (py) and Cu$^{2+}$.

(Synchrotron X-ray Diffraction Measurement)

The synchrotron X-ray diffraction data was obtained at room temperature at beamline BL13XU (with a wavelength of 1.554 angstroms) in Spring-8. During the measurement, helium gas was supplied to a measurement cell.

FIG. 6(a) to (c), FIG. 7(a), FIG. 7(b), and FIG. 8 show the results of the X-ray diffraction measurements of the three-dimensional structure formed on the silicon substrate. The three-dimensional structure was formed by repeating the above-mentioned cycle 20 times.

Figure 6:
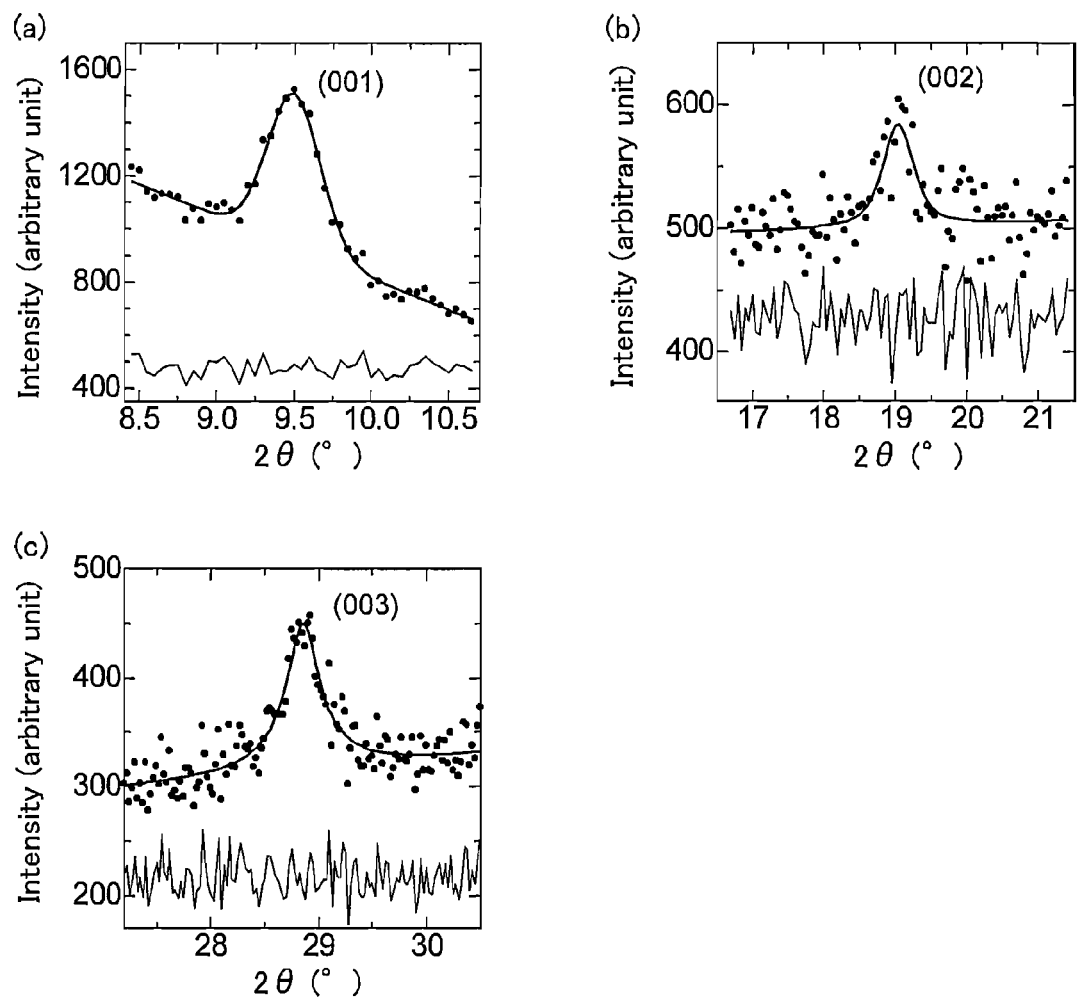
FIGS. 6($a$) to ($c$) show an example of the result of an X-ray diffraction measurement of a three-dimensional structure formed on a silicon substrate.

FIG. 6(a) to (c) show the results of out-of-plane X-ray diffraction (XRD). In the diagram, filled circles represent measured values, and solid lines plotted along the filled circles represent fitting curves. Solid lines below the fitting curves represent differences between the measured values and the fitting curves. The spacing between neighboring two-dimensional structures was calculated from the (001) Bragg reflection at 2θ=9.50°, and was 0.938 nm. The total thickness of the three-dimensional structure was calculated from the full width at half maximum (FWHM) of the peaks, and was 20 nm. This value is in good agreement with the value (0.938 nm×20≈19 nm) obtained when 20 two-dimensional structures are stacked in layers.

Figure 7:
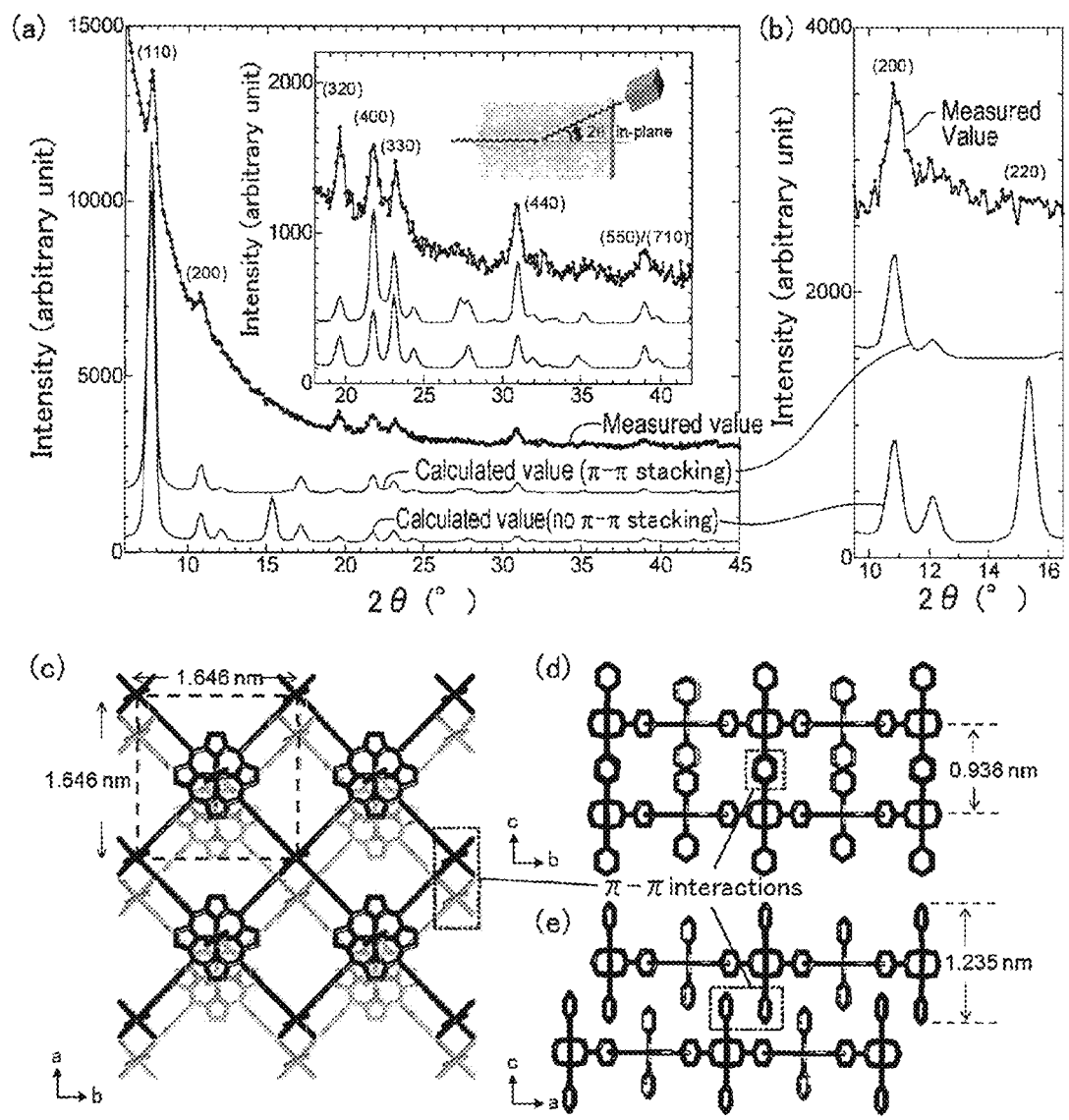
FIGS. 7($a$) and ($b$) show actual measured values and calculated values in an X-ray diffraction measurement.
Figure 8:
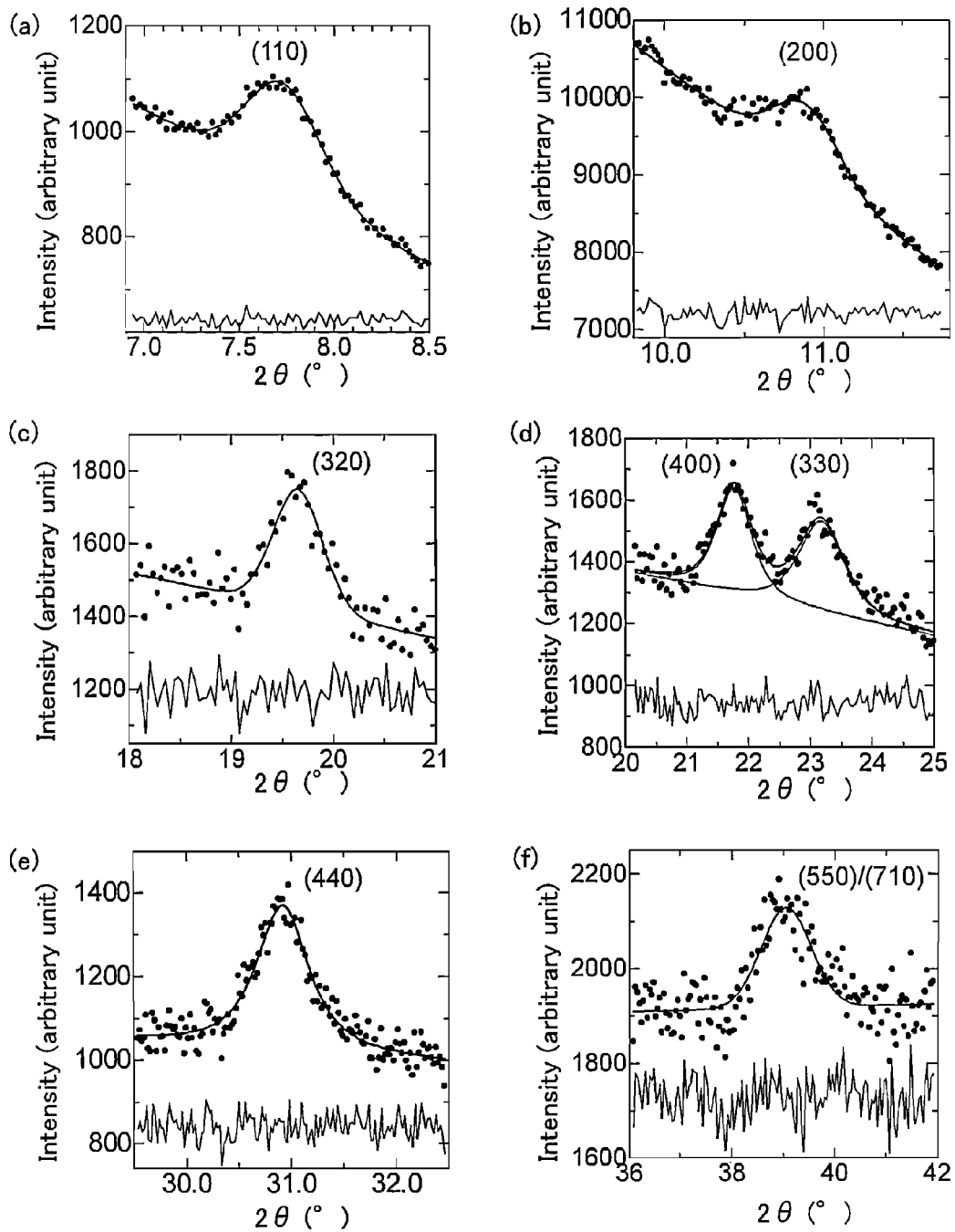
FIGS. 8($a$) to ($f$) show another example of the result of an X-ray diffraction measurement of a three-dimensional structure formed on a silicon substrate.

FIG. 7(a) shows the results of in-plane synchrotron X-ray diffraction. FIG. 7(b) is a diagram showing a selected portion of FIG. 7(a). FIG. 7(a) also shows the values calculated on the assumption that there is π-π stacking and the values calculated on the assumption that there is no π-π stacking.

FIG. 8(a) to (f) show the results of high-statistics fine scans of in-plane grazing incidence X-ray diffraction (GIXRD). In FIG. 8(a) to (f), filled circles represent measured values, and solid lines plotted along the filled circles represent fitting curves. Solid lines below the fitting curves represent differences between the measured values and the fitting curves.

In the in-plane X-ray diffraction, only the (hk0) peaks were observed. On the other hand, in the out-of-plane X-ray diffraction, only the (hk1) (1≠0) peaks were observed.

The average domain size of the crystal was calculated to be about 18 nm from the X-ray diffraction results. On the other hand, the image of the atomic force microscope shows that the domain size is about 20 nm, which means that the X-ray diffraction results and the results of observation with the atomic force microscope were in good agreement.

Figure 9:
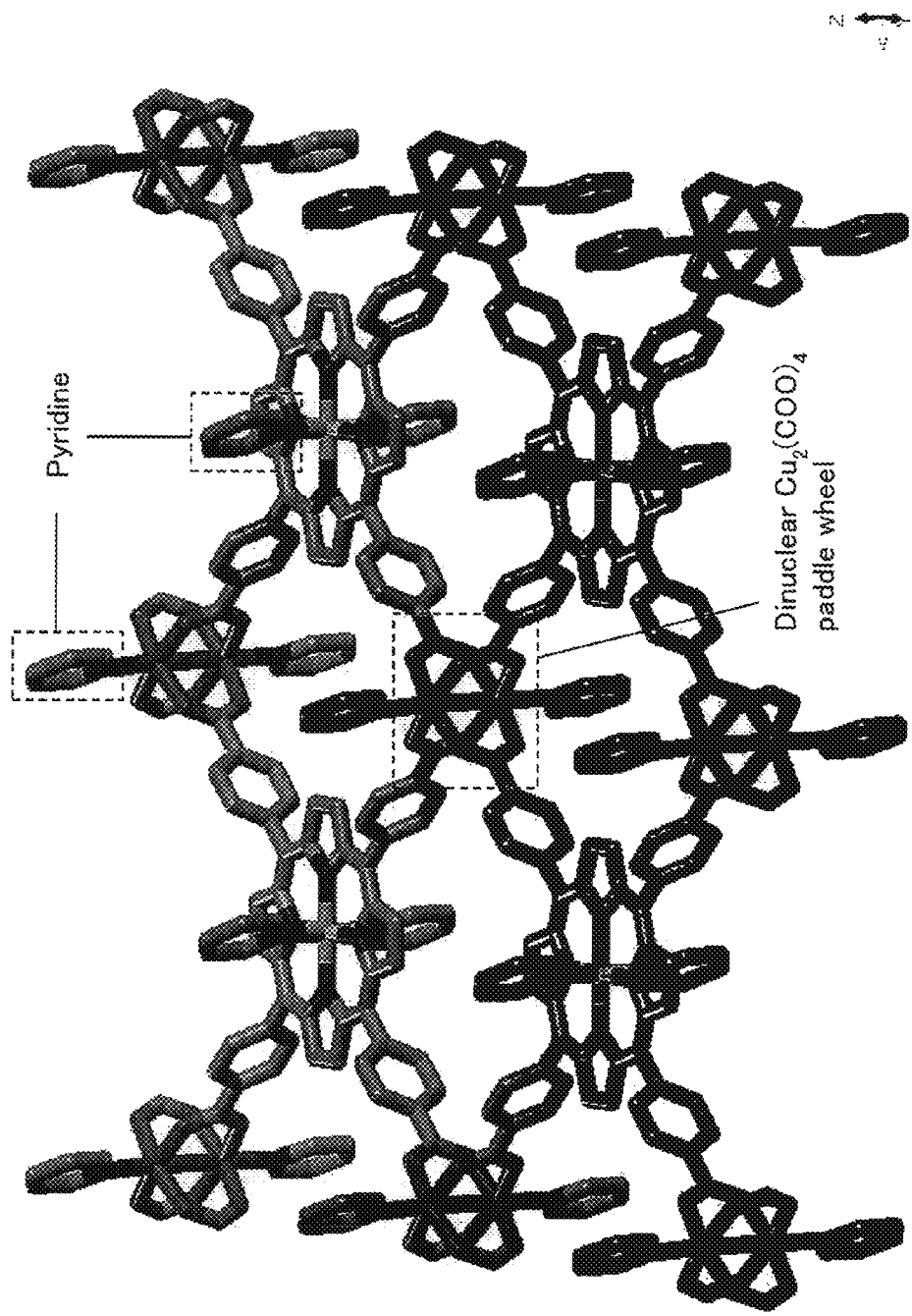
FIG. 9 schematically shows a model of a three-dimensional structure.

FIG. 7(c), FIG. 7(d), FIG. 7(e), and FIG. 9 show one example of the predicted structural model of the three-dimensional structure. FIG. 7(c) shows the structure viewed in a direction parallel to the a-b axis direction. FIG. 7(d) shows the structure viewed in a direction parallel to the b-c axis direction. FIG. 7(e) shows the structure viewed in a direction parallel to the a-c axis direction. FIG. 9 shows a perspective view thereof. It should be noted that the values calculated on the assumption that there is π-π stacking shown in FIG. 7(a) and (b) are the calculated values for this model.

In the illustrated model, the CoTCPP units are linked by dinuclear $Cu_2(COO)_4$ paddle wheels. In this model, each side of each CoTCPP is coordinated with one pyridine (a monodentate ligand). Each side of each dinuclear copper block is also coordinated with one pyridine. The heterocycles of the pyridines are oriented in a direction approximately perpendicular to the direction in which the two-dimensional structure extends. In the illustrated model, the two-dimensional structures are linked by π-π interactions between the pyridines coordinated to the dinuclear paddle wheels (FIG. 7(c) to (e)).

As shown in FIG. 7(a), the calculated values for this model (the values calculated on the assumption that there is π-π stacking) include only the (ht0) peaks, and are in good agreement with the measured values. The spacing between the two-dimensional structures in this model also is in good agreement with the measured spacing thereof (0.938 nm).

The details of the mechanism for the π-π interactions between pyridines are not known. In one hypothesis, the π-π interactions may not occur in the two-dimensional structure immediately after the transfer to the base. Instead, the π-π interactions may occur in the step (Step (x)) of immersing the two-dimensional structure in a solvent sometime after the transfer.

(Study of Step (i))

The first solution used in the step (i), i.e., a solution in which a metal salt is dissolved, was studied. Specifically, two-dimensional structures were formed by dissolving various types of metal salts with various concentrations in the first solution. The first metal ions are supplied by dissolving a metal salt in the first solution.

As the metal salt, cupric chloride dihydrate ($CuCl_2.2H_2O$), nickel (II) chloride hexahydrate ($NiCl_2.6H_22$), or nickel (II) nitrate hexahydrate ($Ni(NO_3)_2.6H_2O$) was used. That is, as the first metal ion, divalent copper ion or divalent nickel ion was used. As the second solution to be spread (the solution to be spread) on the first solution, the same solution as in Example 1, i.e., a solution containing a porphyrin metal complex and pyridine was used. As the porphyrin metal complex, CoTCPP or PdTCPP obtained by replacing the central metal ion of CoTCPP by a palladium ion was used.

The second solution was spread on the first solution by the same method as in Example 1. Next, two barriers were moved in the same manner as in Example 1, and thus a film (a two-dimensional structure) was formed on the surface of the first solution. Then, the area of the film at a surface pressure of 5 mN/m was measured, and the area per porphyrin metal complex molecule was calculated from this measured area and the amount of the porphyrin metal complex in the second solution. Next, the film formed on the surface of the first solution was transferred to a substrate by the same method as in Example 1. Then, it was examined by X-ray diffraction whether or not the first metal ions were deposited on the film transferred to the substrate in the form of the original metal salt which has not reacted with the second solution. Only some of the films were subjected to this examination. Table 1 shows the experimental results and measurement results.

TABLE 1

| | Type of porphyrin metal complex | Type of metal salt | Concentration of metal salt (mmol/L) | Area per porphyrin metal complex molecule ($nm^2$) | Presence or absence of metal salt deposition |
|---|---|---|---|---|---|
| Experiment 1 | CoTCPP | $CuCl_2 \cdot 2H_2O$ | 1 | 1.4 | Not deposited |
| Experiment 2 | CoTCPP | $CuCl_2 \cdot 2H_2O$ | 5 | 1.4 | Not deposited |
| Experiment 3 | CoTCPP | $CuCl_2 \cdot 2H_2O$ | 10 | 1.4 | Unexamined |
| Experiment 4 | CoTCPP | $CuCl_2 \cdot 2H_2O$ | 50 | 1.4 | Unexamined |
| Experiment 5 | CoTCPP | $CuCl_2 \cdot 2H_2O$ | 100 | 1.4 | Deposited |
| Experiment 6 | CoTCPP | $NiCl_2 \cdot 6H_2O$ | 5 | 1.3 | Unexamined |
| Experiment 7 | CoTCPP | $NiCl_2 \cdot 6H_2O$ | 10 | 1.3 | Unexamined |
| Experiment 8 | CoTCPP | $NiCl_2 \cdot 6H_2O$ | 100 | 1.3 | Unexamined |
| Experiment 9 | CoTCPP | $Ni(NO_3)_2 \cdot 6H_2O$ | 100 | 1.2 | Unexamined |
| Experiment 10 | CoTCPP | $CuCl_2 \cdot 2H_2O$ | 0.1 | 0.6 | Unexamined |
| Experiment 11 | CoTCPP | Not used (pure water) | 0 | 0.6 | Not deposited |
| Experiment 12 | PdTCPP | Not used (pure water) | 0 | 0.6 | Not deposited |

In Table 1, "not deposited" means that no X-ray diffraction peak corresponding to a metal salt used as a source material for the first metal ion solution was observed, and "deposited" means that the X-ray diffraction peak was observed.

In Experiments 1 to 9, the areas per porphyrin metal complex molecule at a surface pressure of 5 mN/m fell within the range of 1.2 to 1.4 $nm^2$. On the other hand, when the concentration of the metal salt in the first solution was 0.1 mmol/L or less, the areas occupied by the porphyrin metal complex decreased significantly. This seems to suggest that the two-dimensional structure was not properly formed in some portions. Furthermore, no deposition of the metal salt was observed when the concentrations of the metal salt were in the range of 1 mmol/L to 5 mmol/L. The deposition of the metal salt as a source material may cause a decrease in the surface coverage of the intended three-dimensional structure on the substrate, resulting in a decrease in the properties thereof. These results suggest that the concentration of metal ions in the first solution is preferably in the range of 1 mmol/L to 100 mmol/L, and particularly preferably in the range of 1 mmol/L to 5 mmol/L.

INDUSTRIAL APPLICABILITY

The three-dimensional structure obtained by the present invention can be used for organic devices, catalysts, electrodes, etc.

The invention claimed is:

1. A three-dimensional structure formed on a base, comprising stacked two-dimensional structures, wherein
each of the two-dimensional structures is placed so that its in-plane direction is parallel to a surface of the base,
the two-dimensional structure comprises a plurality of porphyrins, a plurality of first metal ions, and a plurality of specific organic molecules,
the porphyrin comprises two or more carboxyl groups,
the first metal ion is a metal ion that links the carboxyl group of one porphyrin to the carboxyl group of another porphyrin adjacent to each other,
the specific organic molecule is an organic molecule that forms a coordinate bond with a metal ion contained in the two-dimensional structure, that has only one site to coordinate to the metal ion, that contains a π electron, and that comprises a nitrogen-containing aromatic ring,
the porphyrins are cross-linked by dinuclear paddle wheel structures, each dinuclear paddle wheel structure consisting of four carboxyl groups and two first metal ions,
each side of each of the dinuclear paddle wheel structures is coordinated with one specific organic molecule, wherein the each side is in a perpendicular direction relative to a plane defined by the two-dimensional structures in which the dinuclear paddle wheel structures are present, and
the two-dimensional structure is linked to other two-dimensional structures that are located directly above and below therefrom by π-π interactions between the specific organic molecules, which are coordinated to the each side of each of the dinuclear paddle wheel structures in each of the two-dimensional structures.

2. The three-dimensional structure according to claim 1, wherein the porphyrin is a porphyrin containing four carboxyl groups but not containing a central metal ion coordinated to a porphine ring, or is a porphyrin metal complex containing four carboxyl groups and a central metal ion coordinated to a porphine ring.

3. The three-dimensional structure according to claim 2, wherein
the first metal ion is divalent copper ion or divalent nickel ion, and
the specific organic molecule is a molecule containing a nitrogen-containing aromatic ring.

4. The three-dimensional structure according to claim 3, wherein the specific organic molecule is pyridine.

5. The three-dimensional structure according to claim 1, wherein the porphyrin is a porphyrin metal complex containing four carboxyl groups and a cobalt ion coordinated to a porphine ring.

6. A method of producing a three-dimensional structure, comprising steps of:

(i) forming a two-dimensional structure on a surface of a liquid;
(ii) depositing the two-dimensional structure on a base so that its in-plane direction is parallel to a surface of the base;
(x) immersing the base on which the two-dimensional structure is deposited into a solvent; and
(iii) repeating a cycle including the step (i), the step (ii), and the step (x) once or more,
wherein the two-dimensional structure comprises a plurality of porphyrins, a plurality of first metal ions, and a plurality of specific organic molecules,
the porphyrin contains two or more carboxyl groups,
the first metal ion is a metal ion that links the carboxyl group of one porphyrin to the carboxyl group of another porphyrin adjacent to the one porphyrin,
the specific organic molecule is an organic molecule that forms a coordinate bond with a metal ion contained in the two-dimensional structure, that has only one site to coordinate to the metal ion, that contains a π electron, and that comprises a nitrogen-containing aromatic ring,
the porphyrins are cross-linked by dinuclear paddle wheel structures, each dinuclear paddle wheel structure consisting of four carboxyl groups and two first metal ions,
each side of each of the dinuclear paddle wheel structures is coordinated with one specific organic molecule, wherein the each side is in a perpendicular direction relative to a plane defined by the two-dimensional structures in which the dinuclear paddle wheel structures are present, and
the two-dimensional structure is linked to other two-dimensional structures that are located directly above and below therefrom by π-π interactions between the specific organic molecules, which are coordinated to the each side of each of the dinuclear paddle wheel structures in each of the two-dimensional structures.

7. The production method according to claim 6, wherein the porphyrin is a porphyrin containing four carboxyl groups but not containing a central metal ion coordinated to a porphine ring, or is a porphyrin metal complex containing four carboxyl groups and a central metal ion coordinated to a porphine ring.

8. The production method according to claim 7, wherein
the first metal ion is divalent copper ion or divalent nickel ion, and
the specific organic molecule is a molecule containing a nitrogen-containing aromatic ring.

9. The production method according to claim 8, wherein the specific organic molecule is pyridine.

10. The production method according to claim 6, wherein the porphyrin is a porphyrin metal complex containing four carboxyl groups and a cobalt ion coordinated to a porphine ring.

11. The production method according to claim 6, wherein the step (i) is a step of forming the two-dimensional structure on the surface of the liquid by adding a second solution containing the porphyrins and the specific organic molecules to a first solution containing the first metal ions.

12. The production method according to claim 6, wherein the step (ii) is a step of bringing the base closer to the two-dimensional structure, with the surface of the base kept parallel to the surface of the liquid, and thereby depositing the two-dimensional structure on the base.

* * * * *